United States Patent
Boyden et al.

(10) Patent No.: US 8,851,072 B2
(45) Date of Patent: Oct. 7, 2014

(54) SUPPLEMENTAL AIR DIFFUSION DEVICES, KITS AND METHODS

(75) Inventors: Marc S. Boyden, Salt Lake City, UT (US); John H. Matsen, Salt Lake City, UT (US)

(73) Assignee: Wasatch Manufacturing, LLC, Salt Lake City, UT (US)

( * ) Notice: Subject to any disclaimer, the term of this patent is extended or adjusted under 35 U.S.C. 154(b) by 2087 days.

(21) Appl. No.: 11/675,948

(22) Filed: Feb. 16, 2007

(65) Prior Publication Data

US 2008/0196719 A1    Aug. 21, 2008

(51) Int. Cl.
*A61M 16/00* (2006.01)
*A62B 9/00* (2006.01)
*A61M 16/06* (2006.01)

(52) U.S. Cl.
CPC ....... *A61M 16/00* (2013.01); *A61M 2202/0208* (2013.01); *A61M 16/06* (2013.01); *A61M 16/0683* (2013.01); *A61M 2209/06* (2013.01)
USPC ................................ 128/204.18; 128/200.24

(58) Field of Classification Search
CPC ..................... A61M 2016/00; A61M 2016/06; A61M 2016/0661; A62B 7/00; A62B 7/02; A62B 7/12; A62B 9/00
USPC ............ 128/200.24, 200.29, 203.12–203.13, 128/203.25, 203.28–203.29, 204.18, 128/205.25, 205.27–206.21
See application file for complete search history.

(56) References Cited

U.S. PATENT DOCUMENTS

| | | | |
|---|---|---|---|
| 2,954,027 A | | 9/1960 | Marasco .................. 128/206.28 |
| 3,682,171 A | * | 8/1972 | Dali et al. ................ 128/207.18 |
| 3,683,907 A | * | 8/1972 | Cotabish .................. 128/200.28 |
| 3,806,100 A | * | 4/1974 | Cornett et al. ..................... 261/1 |
| 3,894,537 A | | 7/1975 | Camp |
| 3,949,743 A | | 4/1976 | Shanbrom |
| 4,669,461 A | | 6/1987 | Battaglia et al. .......... 128/202.15 |
| 4,804,026 A | | 2/1989 | Bailey ............................ 141/340 |
| 4,823,848 A | | 4/1989 | Sentmore, Sr. et al. ....... 141/334 |
| 4,848,334 A | | 7/1989 | Bellm |
| 4,955,372 A | | 9/1990 | Blackmer et al. |

(Continued)

FOREIGN PATENT DOCUMENTS

| | | | | |
|---|---|---|---|---|
| DE | 228504 | | 10/1985 | .............. A61B 5/08 |
| DE | 10011240 | | 3/2000 | .............. B62J 39/00 |

(Continued)

*Primary Examiner* — Rachel Young
(74) *Attorney, Agent, or Firm* — Workman Nydegger

(57) ABSTRACT

A supplemental air diffusion device is shaped and configured to be attached to the body or clothing of a patient below the head and deliver supplemental air toward the mouth and nose of the patient. The supplemental air diffusion device includes a frustroconicoidal air diffusion body that has a smaller inlet opening at an inlet end and an enlarged diffusion opening at a diffusion end. An air inlet stem is integrally attached to the air diffusion body and includes a plurality of ribs and/or recesses for releasably locking a female connector of an air supply hose over the inlet stem. A pair of spaced-apart slits are provided through a flange extending laterally from an outer surface of the air diffusion device. Initially separate accessory patient attachment clamps are looped through the slits and provide for releasable attachment of the air diffusion device to a patient's clothing. A kit may include an air diffusion device, one or more accessory patient attachment clamps, and an air supply hose for establishing fluid communication between the air diffusion device and an air supply.

12 Claims, 8 Drawing Sheets

(56) References Cited

U.S. PATENT DOCUMENTS

| | | | |
|---|---|---|---|
| 4,971,271 A * | 11/1990 | Sularz | 248/68.1 |
| 5,533,513 A | 7/1996 | Ueda et al. | 600/543 |
| 5,758,642 A | 6/1998 | Choi | |
| 5,765,553 A | 6/1998 | Richards et al. | |
| 5,890,516 A * | 4/1999 | Talamonti | 137/605 |
| D434,141 S | 11/2000 | Randeberg et al. | D24/110.4 |
| 6,237,596 B1 * | 5/2001 | Bohmfalk | 128/206.22 |
| 6,273,087 B1 | 8/2001 | Boussignac et al. | 128/204.22 |
| 6,588,420 B1 * | 7/2003 | Burch | 128/200.24 |
| 6,739,363 B2 | 5/2004 | Walter et al. | 141/331 |
| D499,803 S | 12/2004 | Chang | D24/110.4 |
| 6,843,717 B1 * | 1/2005 | Bennett | 454/152 |
| 7,004,168 B2 | 2/2006 | Mace et al. | 128/206.21 |
| 2004/0216745 A1 * | 11/2004 | Yuen et al. | 128/205.27 |
| 2005/0022286 A1 * | 2/2005 | Noble et al. | 2/69 |
| 2005/0081850 A1 * | 4/2005 | Watt et al. | 128/203.12 |
| 2005/0109344 A1 * | 5/2005 | Cook | 128/207.14 |
| 2006/0076021 A1 * | 4/2006 | Chang | 128/207.15 |
| 2006/0196510 A1 | 9/2006 | McDonald et al. | |
| 2006/0283461 A1 * | 12/2006 | Lubke et al. | 128/207.11 |
| 2008/0072910 A1 * | 3/2008 | Janbakhsh et al. | 128/206.27 |
| 2008/0134474 A1 * | 6/2008 | Uryasov | 24/303 |

FOREIGN PATENT DOCUMENTS

| | | | |
|---|---|---|---|
| EP | 1234541 | 8/2002 | A61B 5/083 |
| JP | 09019506 | 1/1997 | A62B 9/04 |
| JP | 09262224 | 10/1997 | A61B 5/08 |
| RU | 2031747 | 3/1995 | B08B 15/00 |

* cited by examiner

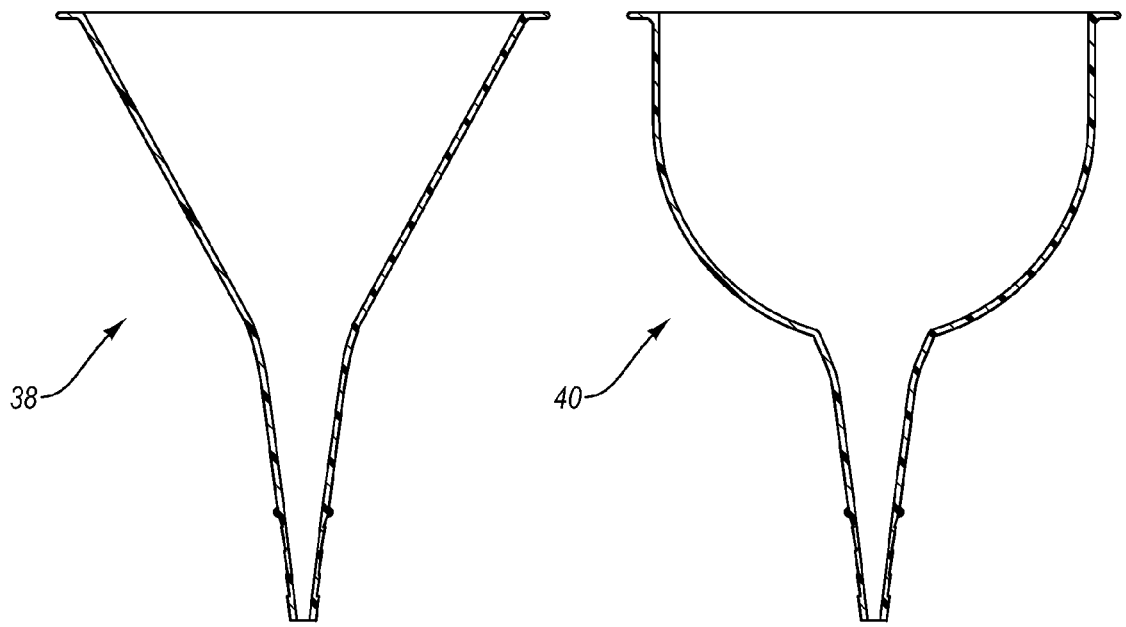
*Fig. 5A*  *Fig. 5B*
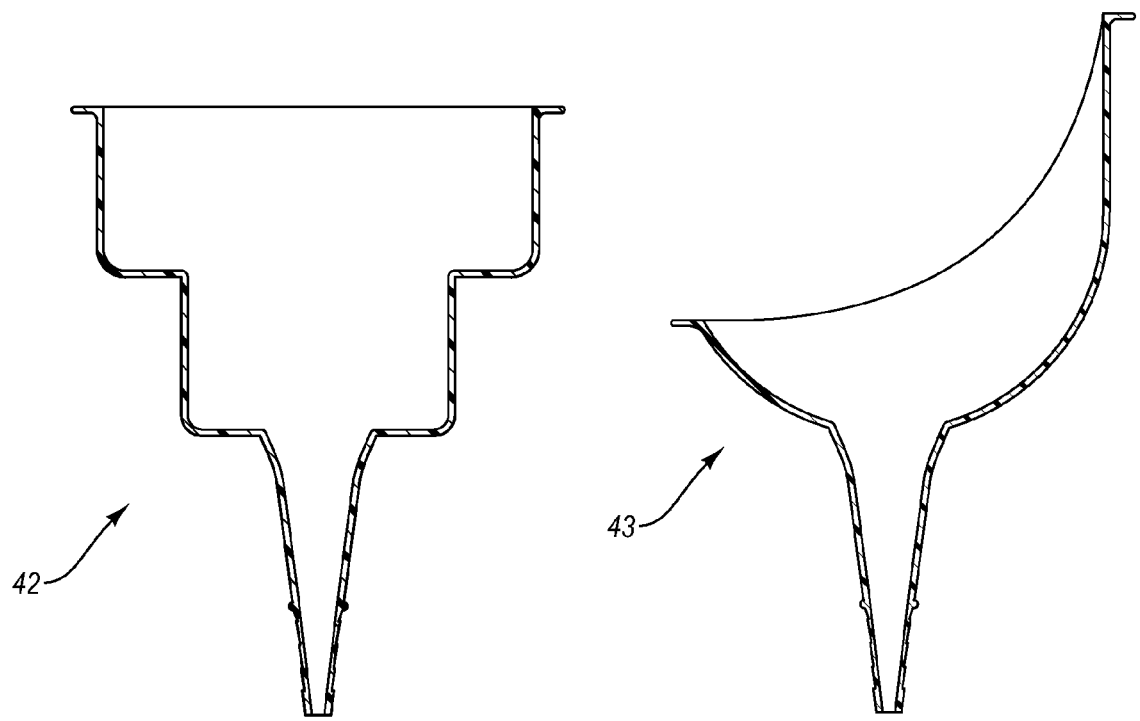
*Fig. 5C*  *Fig. 5D*

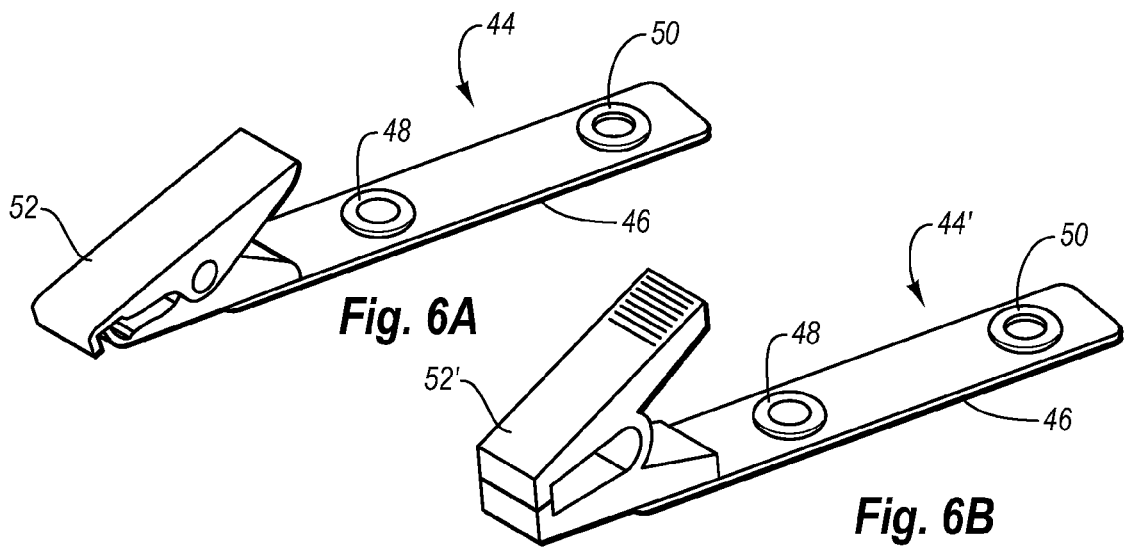
Fig. 6A
Fig. 6B
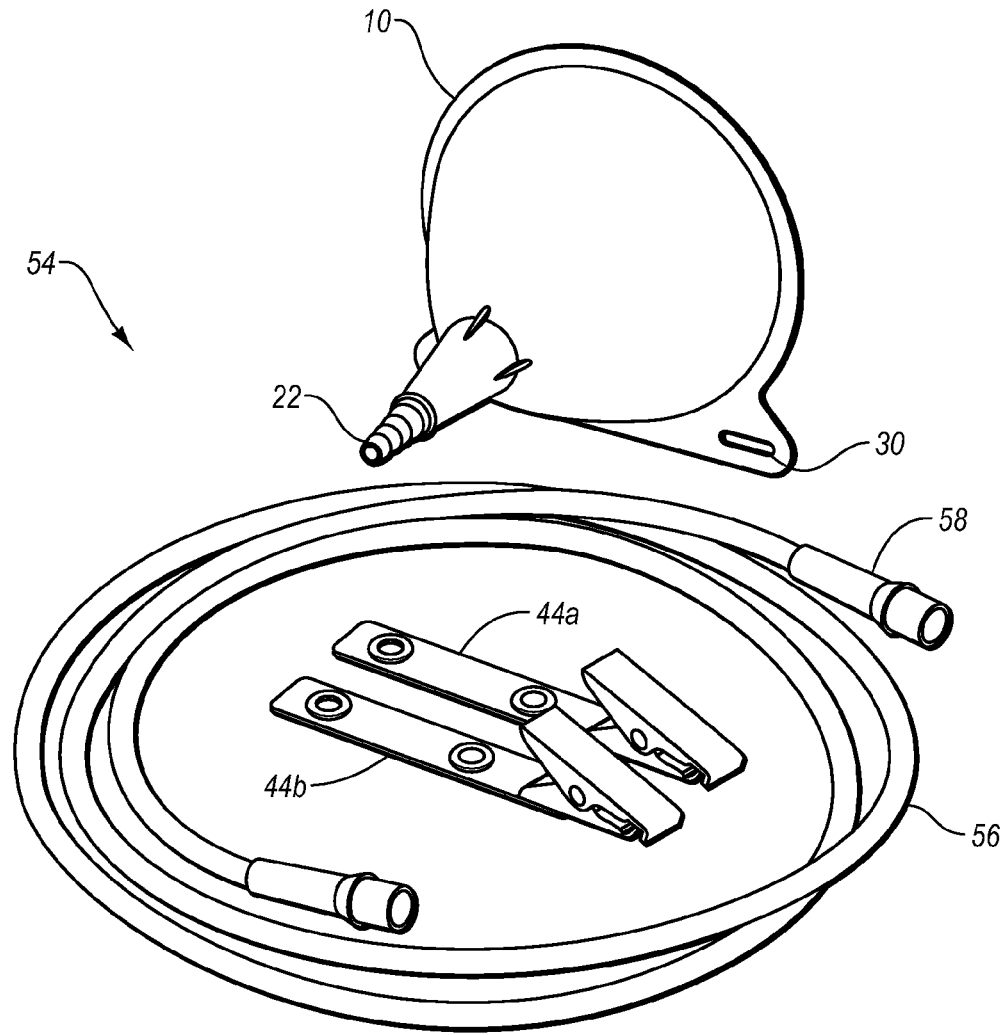
Fig. 7

SUPPLEMENTAL AIR DIFFUSION DEVICES, KITS AND METHODS

BACKGROUND OF THE INVENTION

1. The Field of the Invention

The present invention relates to diffusion devices, kits and methods for delivering supplemental air to a patient.

2. The Relevant Technology

Maintaining a sufficient oxygen supply is critical to sustaining human life. While most people can easily obtain sufficient oxygen through normal breathing of ambient air, there are circumstances where ordinary breathing cannot provide adequate oxygen. Patients are often given supplemental air enriched with oxygen. The need for supplement air can be caused by many different conditions, including lung disease, trauma, hazards such as smoke inhalation, and premature birth. Supplemental air can also be used to deliver a medicament to a patient.

Supplemental air is typically administered by delivering oxygenated air from a tank to the mouth and/or nose of the person. There are two principle ways supplemental air is administered to a person. One technique uses an oxygen mask that covers the person's nose and mouth. The oxygen mask typically allows the person to breathe surrounding air while delivering supplemental air to the space between the mask and the patient's face. The supplemental air mixes with the air being inhaled to ensure adequate oxygenation of the patient. Oxygen masks are commonly made of a translucent plastic. They typically have a connector on the outside that allows a hose to be attached and an outlet on the inside of the mask for delivering the supplemental air. They may have an elastic cord that wraps around the back of the head to secure the mask to the patient.

While oxygen masks are very effective at delivering supplemental air to a patient, they can be uncomfortable, awkward, unsightly, and pose health risks for some patients. Some patient's can feel claustrophobic or anxious when hoses and/or devices are attached to their face or head. Infants and young children tend to pull them off as they are typically averse to objects covering their faces. Adults might use them while in a hospital, bedridden or otherwise out of sight of others, but may be averse to wearing them in public, particularly in social settings where they may draw negative attention and cause embarrassment. Masks muffle speech and inhibit normal conversation. From a safety standpoint, masks that cover the patient's face can make it difficult for caretakers to discover foreign objects or debris, such as food, vomit or mucous, that might be accidentally inhaled by the patient or that might obstruct the diffusion of supplement air To avoid some of the problems associated with masks, patients can be given supplemental air through a nasal device, i.e., tubes inserted into the nostrils and taped to the patient's face. Rather than covering the entire mouth and nose, the nasal device delivers supplemental air to only the nose. Nasal air delivery devices permit viewing of the mouth and allow the patient to talk more easily. However, such devices require nasal breathing by the patient to obtain supplemental air. Nasal delivery devices also suffer from negative social stigma, as they are both unsightly and emit audible bursts of air. Infants and young children tend to rip the tubes out of their noses, thereby destroying their effectiveness.

One attempt to avoid the disadvantages of masks and nasal devices utilizes a food grade funnel jerry-rigged with a universal connector stuffed into the smaller end, often with the aid of tape to hold it in place, to which is attached a hose that supplies oxygen enriched supplemental air. This improvised funnel device is laid on the chest of an infant and supplemental air is blown out the enlarged funnel opening toward the face of the infant.

Because the improvised funnel device does not cover the infant's face, infants do not notice it and tend to leave it in place, at least while sleeping on their backs. However, even small movements can cause the improvised funnel device to fall off the infant's chest, creating a dangerous situation for infants who require supplemental air to live. Consequently, the improvised funnel device generally cannot be used while the infant is awake or otherwise prone to move. It requires careful attention and/or frequent monitoring by a health care provider. Unless taped to a patient's body (e.g., by winding surgical tape around the funnel and patient's chest), the device cannot be used by a patient in a sitting, standing or other upright position, but only while supine on the patient's back. Tape may not always stick well to a patient's shirt, or it may stick too well and leave adhesive residue.

Another problem with the improvised funnel device is that the universal connector is merely provisionally attached and can easily become detached or leak. Leakage can cause waste and/or result in insufficient supplemental air reaching the patient. Detachment can result in total cessation of supplemental air to the patient, which can result in harm or death.

In view of the foregoing, there is a tremendous need, long felt in the art, to provide improved devices and methods for delivering supplemental oxygen to a patient.

BRIEF SUMMARY OF THE INVENTION

The present invention relates to supplemental air diffusion devices that overcome some or all of the aforementioned problems. The supplemental air diffusion devices include an inlet stem to which a supplemental air hose can be attached, a frustroconicoidal diffusion body integrally attached to the inlet stem, and attachment means on the diffusion body for attaching accessory patient attachment devices to the diffusion body. The invention provides for ready and secure attachment of the diffusion device to a patient while in many different positions, reliable diffusion of supplemental air to the patient without the risk of leaking or detachment of the inlet stem, and easy removal of the device from the patient. The diffusion device can be attached so as to not block or cover any part of the patient's face (e.g., on the chest below the neck).

The inlet stem of the diffusion device advantageously includes coupling means for releasably locking a female coupler of an air supply hose thereto. In one embodiment, the coupling means comprise a plurality of ribs and/or recesses formed on an outer surface of the inlet stem. In use, the ribs and/or recesses on the inlet stem form a male connector which interlocks with one or more corresponding ribs and/or recesses associated with an inner surface of a female connector on an end of the air supply hose. The inlet stem can be tapered to permit progressively tighter fit between the inlet stem and the female air supply hose connector as the female connector is inserted over the inlet stem. The inlet stem may include a stop, such as an annular ridge, that limits the distance the inlet stem can be inserted into the female connector.

The inlet stem is advantageously formed integrally with the frustroconicoidal diffusion body to prevent the inlet stem from becoming detached during use. The diffusion device may include stiffening means for preventing bending or collapse of the inlet stem relative to the diffusion body while inserting the inlet stem into the female connector of the air supply hose. An example of stiffening means are one or more raised stiffening ribs molded into the surface of, and bridging the interface between, the diffusion body and inlet stem. The stiffening means can also prevent bending or detachment of the inlet stem from the diffusion body while attached to and/or being removed from the female connector of the air supply hose.

The diffusion body is generally frustroconicoidal and has a smaller inlet opening at one end into which supplemental air is introduced from the inlet stem and an intermediate body portion that expands to an enlarged diffusion opening through which the supplemental air can be diffused toward a patient's face. The increase in size of the frustroconicoidal diffusion body from the smaller inlet opening to the enlarged diffusion opening causes a decrease in velocity of the supplement air stream as it diffuses to fill the volume of the diffusion body. An enlarged column of supplement air exits the diffusion opening and moves toward the vicinity of the patient's mouth and nose at a controlled velocity.

The attachment means provide for attachment of one or more accessory patient attachment devices to the diffusion device. Examples of means for attaching an accessory patient attachment device to the diffusion device include one or more slits, holes, snaps, Velcro®, adhesive, permanent weld, or combinations thereof formed on the air diffusion body and/or on a flange extending laterally from the air diffusion body.

The accessory patient attachment devices are configured and provide means for removably attaching the diffusion device to a patient. Examples of accessory patient attachment devices and means for removably attaching the diffusion device to a patient's include one or more snaps, buttons, clips, clamps, Velcro®, or combinations thereof. The one or more accessory patient attachment devices may be integrally or removably connected to the diffusion device. One example of an accessory patient attachment device comprises a spring-loaded clamp that clips onto a patient's clothing and a flexible strap that can be attached to the diffusion device (e.g., by being looped through a recess in the air diffusion body or a recess in a flange extending laterally from a side of the diffusion body). The flexible strap includes a snap, Velcro® or other interlocking feature for securing the strap to the diffusion device. The accessory patient attachment device may also include an elongate strap that can wrap around and provide direct attachment of the diffusion device to the patient's body.

According to one particularly useful embodiment, the attachment means provides for attachment of multiple spaced-apart accessory patient attachment devices to the air diffusion body. This allows the diffusion device to be attached to a patient's body or clothing at spaced-apart points or regions of connection (e.g., 2), which greatly increases positional stability of the device compared to a single point of attachment. Providing multiple points or regions of connection greatly reduces the degree of freedom of movement of the diffusion device compared to a single point of connection, which may allow a diffusion device to flop back and forth in response to patient movements. Reducing the degree of freedom of movement increases comfort to the patient and more reliably directs the supplement air flow toward the person's mouth and nose.

The diffusion device may be advantageously formed from a transparent polymer, which provides greatly improved ability to see if emesis or other foreign debris might have fallen into the diffusion body and/or inlet stem, which could potentially block the flow of supplemental air and compromise the ability of the patient to receive supplemental air.

In an alternative embodiment, the diffusion device may have a pre-attached air supply hose. The supply hose may be removably or integrally attached to the inlet stem of the diffusion device. In one embodiment, the outer wall of the inlet is stepped to provide a smaller outer diameter at the tip and a larger diameter up the wall to increase tightness of fit between the inlet stem and air supply hose. An end of the air supply hose can be attached over and glued or otherwise integrally connect onto the outer wall of the inlet stem. An elongate main portion extends from the inlet end for attachment to an air supply.

The invention also includes a method for delivering supplemental air to a person. The method includes providing a supplemental air diffusion device as described herein, attaching one end of an air supply hose to the inlet stem and another end of the air supply hose to a supplement air supply, and attaching the diffusion device to the clothing or body of a person with the diffusion opening directing supplemental air toward the mouth and nose of the person. In the case where initially separate accessory patient attachment devices are used, they are first attached to the diffusion device and then used to removably attach the device to the patient's clothing or body.

Because the supplemental air diffusion device is securely attached below the person's face, the person can move about and assume different positions without compromising the ability to obtain supplemental air. The ability of the inventive diffusion device to remain in place near a patient's face is particularly beneficial in the case of infants who require supplemental air to stay alive. Compared to conventional masks and nasal tubes, a person can talk and socialize with minimal intrusiveness and does not appear like an obvious invalid, which can greatly improve confidence in social settings.

The invention further includes kits for use in delivering supplemental air to a patient. An exemplary kit includes a supplemental air diffusion device as discussed herein, an air supply hose having a connector at one end for coupling the air supply hose to the inlet stem of the diffusion device, and one or more accessory patient attachment devices as described herein, or which are generally known in the art for use in attaching badges or other devices to a person's clothing, for use in removably and securely attaching the diffusion device to a person's clothing or body.

The inventive devices, kits and methods advantageously allow persons to non-intrusively receive supplemental oxygen without having to wearing a mask over their face or having tubes stuffed into their nose. Such devices, kits and methods can provide supplemental air whether the person is standing or sitting, conscious or unconscious. The inventive devices, kits and methods are particularly advantageous for use with infants and small children because the diffusion device is less likely to be removed by the infant or child as they are not connected to the head or face of the infant or child. The diffusion devices are far more aesthetically pleasing compared to masks or tubes. The devices of the invention also provide improved safety for patients since health care provides can more easily examine the airway of a patient using the device and/or can observe objects that may be blocking the optimal flow of air through the diffusion device. This is particularly true in the case where the device is made from a transparent material.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 5A is a cross-sectional view of the air diffusion device of FIG. 1;

FIG. 5B is a cross-sectional view of an alternative embodiment of a supplemental air diffusion device according to the invention;

FIG. 5C is a cross-sectional view of another alternative supplemental air diffusion device according to the invention;

FIG. 5D is a cross-sectional view of another alternative supplemental air diffusion device according to the invention having an air guiding extension;

FIGS. 6A and 6B illustrate exemplary accessory patient attachment devices that may be used to attach a supplemental air diffusion device to a patient's clothing;

FIG. 7 illustrates a kit that includes a supplemental air diffusion device, accessory patient attachment devices, and an air supply hose tubing configured for coupling the supplement air diffusion device to a supplemental air supply;

DETAILED DESCRIPTION OF THE PREFERRED EMBODIMENTS

The present invention is directed to devices for delivering supplemental air to a patient, methods for using the device, and kits including the device. The supplemental air diffusion device is shaped and configured for attachment to the body or clothing of a patient and to direct supplemental air toward the mouth and nose of a person without being connected over the head or face of the patient.

For purposes of this invention, the term "frustroconicoidal" is strictly not limited to shapes that are precisely defined by the term "frustroconical". Rather, "frustroconicoidal" includes, but is not limited to, conical-like shapes that have a circular or semicircular cross-section, a v-shaped cross-section, a parabolic cross-section, a stepped cross-section, among others.

Figure 1:
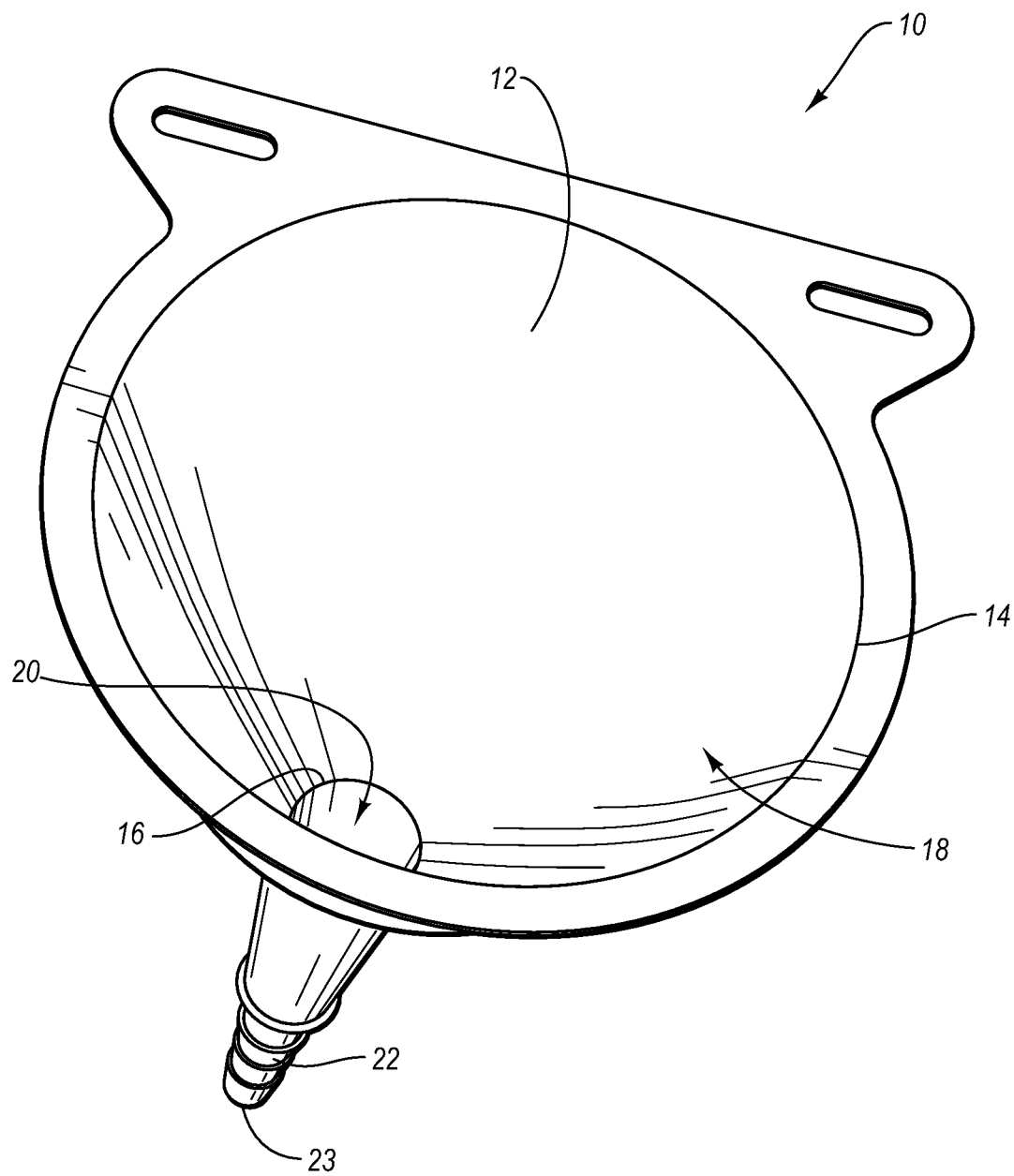
FIG. 1 illustrates a perspective view of a supplemental air diffusion device according to one embodiment of the invention.
Figure 2:
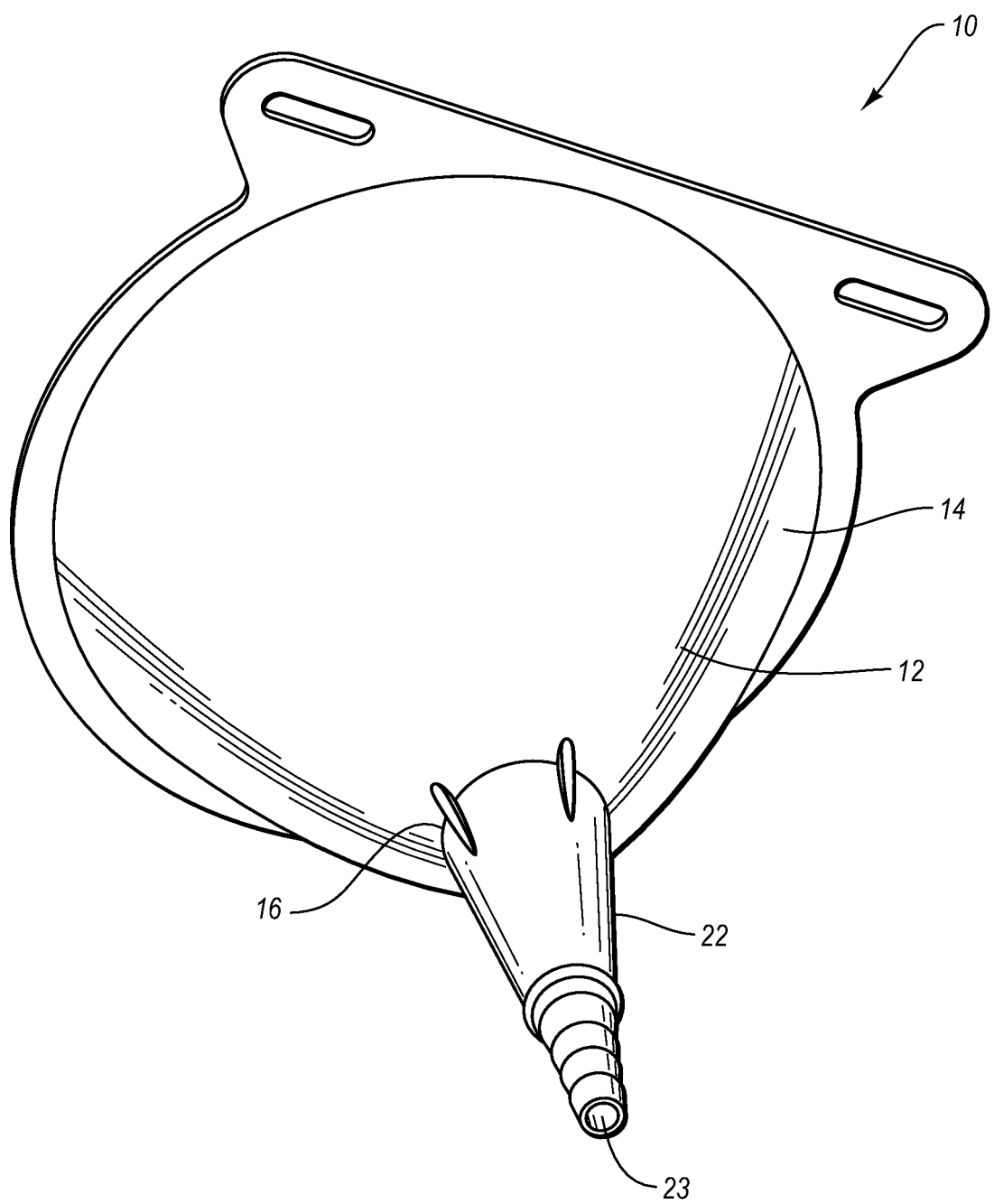
FIG. 2 illustrates a bottom perspective view of the air diffusion device of FIG. 1.

FIGS. 1 and 2 show perspective views of a supplemental air delivery device 10 according to one embodiment of the invention. Supplemental air delivery device 10 includes a frustro-conicoidal air diffusion body 12 having an air diffusion end 14 and an air inlet end 16. Air diffusion end 14 defines an enlarged diffusion opening 18, and air inlet end 16 defines a smaller inlet opening 20. Air diffusion body 12 defines an outer wall that generally increases in size, and bounds an inner passageway, extending between inlet opening 20 and diffusion opening 18.

Integrally attached to diffusion body 12 is an inlet stem 22 proximal to inlet end 16, which includes a stem opening 23 in fluid communication with inlet opening 20. Inlet stem may be tapered on both the inner and outer walls.

Figure 3:
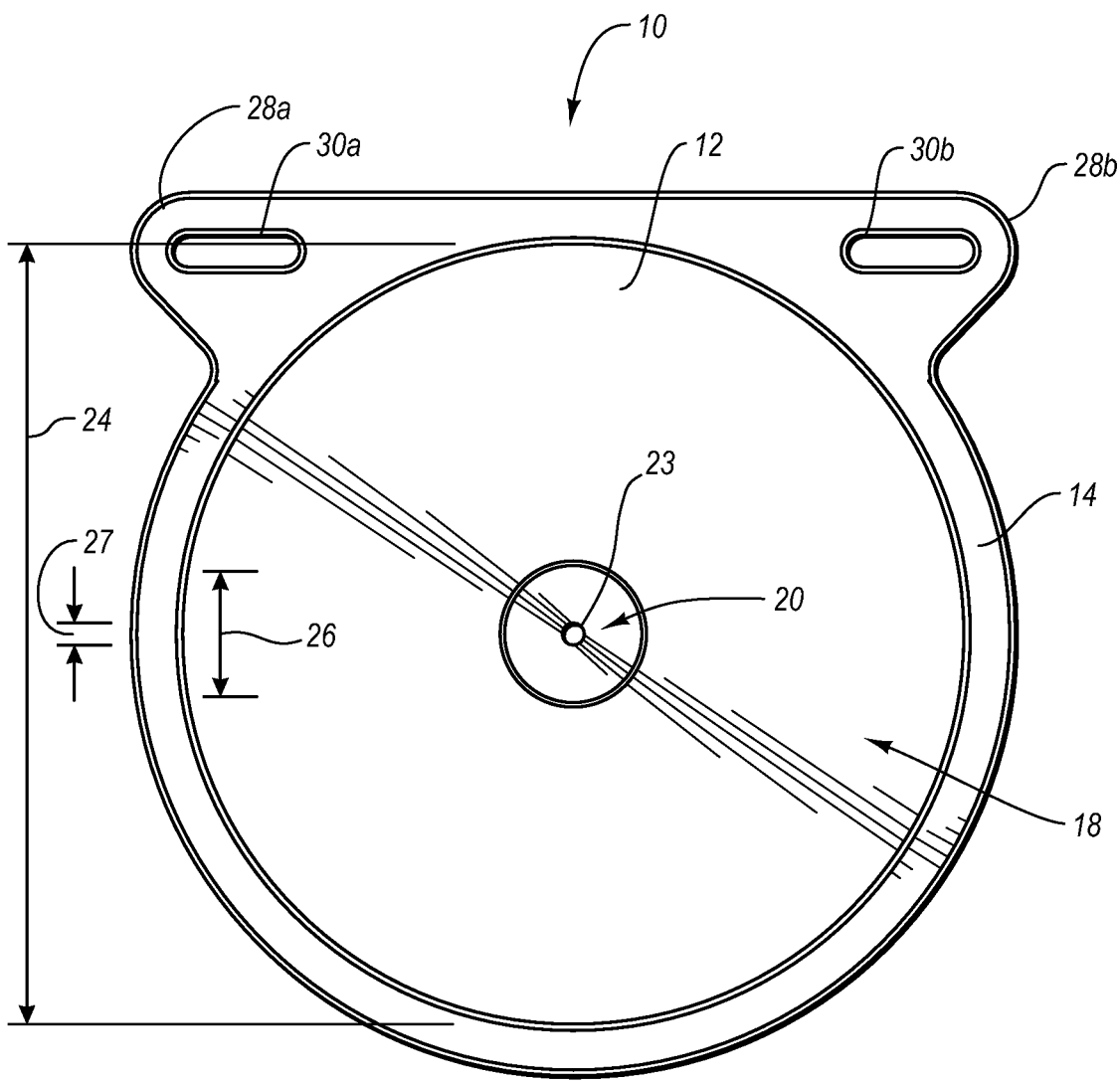
FIG. 3 illustrates a top view of the supplemental air diffusion device of FIG. 1.

Diffusion opening 18 can be any size and shape so long as it is sufficiently large to direct a desired amount of supplemental air toward a patient's face (i.e., mouth and nose). Body 12 increases in size from inlet end 16 toward diffusion end 14. FIG. 3 is a top view of diffusion device 10, illustrating exemplary diameters of the diffusion opening 18, inlet opening 20, and stem opening 23 according to one embodiment of the invention. As shown in FIG. 3, diameter 24 of diffusion opening 18 is substantially larger than diameter 26 of inlet opening 22, which is larger than diameter 27 of stem opening 23. The expansion of body 12 between inlet opening 20 and diffusion opening 18, and to some extent the increasing inner diameter of inlet stem 22, allow the diffusion device to reduce the flow speed of air traveling out of device 10 compared to air flowing into device 10.

The desired diameter of diffusion opening 18 can depend on the volume of air being delivered to the patient and the age of the patient. For example, diffusion openings with smaller diameters are typically used with infants and small children, while larger diameter diffusion openings can be used with older patients. In one embodiment, the diameter 24 of the diffusion opening 18 is greater than 5 cm, more preferably greater than 7.5 cm, and most preferably greater than 10 cm.

The diffusion device 10 also includes one or more flanges (e.g., flanges 28a and 28b) extending from air diffusion body 12. Flanges 28a and 28b include slits or openings 30a and 30b (collectively slits or openings 30). The slits 30 provide means for attaching accessory patient attachment devices to diffusion device 10. Flanges 28 can have any shape or thickness and slits or openings 30 can have any size or shape so long as the openings 30 can be formed in flanges 28.

In a preferred embodiment, device 10 includes at least two flanges for use connecting diffusion device 10 to a patient via accessory patient attachment devices. Providing more than one attachment point for connecting device 10 to the body or clothing of the patient is advantageous as it prevents device 10 from swiveling from side to side when a person wearing the device leans from side to side. In one embodiment, the flanges are proximate to the center of gravity of the device. In another embodiment, the flanges 28 are positioned near the proximal end 14 of the device 10.

Figure 4:
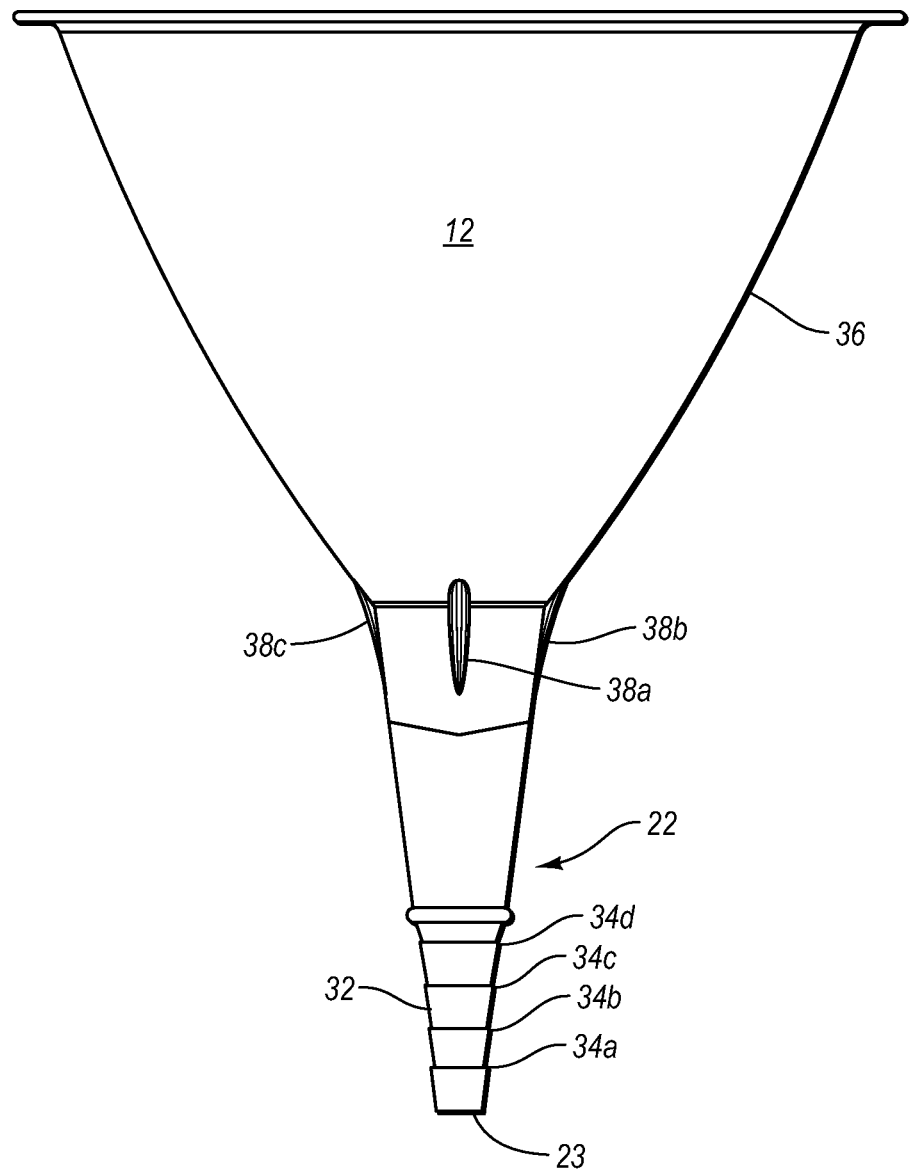
FIG. 4 illustrates a side elevational view of the air diffusion device of FIG. 1.

Turning now to FIG. 4, the air diffusion body is shown having a bell-shaped outer wall portion 36 and inlet stem 22 is shown to include coupling means integrally formed therein. In one embodiment, coupling means 32 include a plurality of ribs 34a-34d. The stem 22 can be tapered and/or the ribs 34 can have an increasing diameter such that the ribs 34 form a tighter fit from the distal toward the proximal rib (i.e., an increasingly tighter fit from rib 34a to 34d) as a connector of an air supply hose is inserted over the inlet stem 22. Ribs 34 can be configured to couple with a female connector 58 of an air supply hose 56 (FIG. 7). In a preferred embodiment, the coupling means 32 are integrally formed into the inlet stem 22 of diffusion device 10 to prevent leaking or inadvertent decoupling during use, as can occur if the coupling means are a separate device attached to inlet stem 22.

FIG. 4 also shows stiffening means, attached to the air diffusion body 12 and air inlet stem 22, for preventing bending or collapse of the inlet stem 22 relative to the diffusion body 12 while inserting the inlet stem 22 into a female connector of an air supply hose. As illustrated, the stiffening means may comprise one or more raised stiffening ribs (e.g., stiffening ribs 38a-38c) molded into the surface of, and bridging the interface between, the diffusion body 12 and inlet stem 22.

Diffusion device 10 is not limited to a device having a conical shape diffusion body. Frustroconicoidal air diffusion body 12 can have any shape with an enlarged opening at the proximal end that tapers to a smaller inlet opening for introducing air. FIGS. 5A-5D provide example alternative embodiments of the invention. FIG. 5A illustrates a device 38 with a conical or substantially v-shaped cross-section. The cross-section of device 38 in FIG. 5A has a generally linear taper. FIG. 5B alternatively shows a device 40 having a substantially parabolic cross-section. FIG. 5C shows a device 42 having a stepped cross-section. FIG. 5D shows a device that also includes an air guiding wall extension built into the air diffusion body in order to help direct air flow toward the patient's mouth and nose.

The invention also extends to frustroconicoidal devices that have shapes other than those illustrated in FIGS. 5A-5D. For example, the diffusion device is not limited to symmetrical cross sections. The diffusion device can have a regular or irregularly shaped horizontal cross-section. In one embodiment, the horizontal cross-section is a circle. Alternatively the horizontal cross-section can be a semicircle.

The diffusion device of the invention may be used in conjunction with one or more accessory patient attachment devices, which are used for attaching the diffusion device to the body or clothing of a patient. FIGS. 6a and 6b illustrate exemplary accessory patient attachment devices 44 and 44' for attaching diffusion device 10 to a patient. Accessory patient attachment devices 44 and 44' include a strap 46, a male snap 48, female snap 50, and a clamp 52. Strap 46 can be secured to flanges 28 by inserting strap 46 into slit or opening 30. Snaps 48 and 50 can then be connected to secure strap 46 to device 10. Clamp 52 or 52' is then available for attachment to clothing on a patient. Strap 46, snaps 48 and 50, and clamps 52 and 52' can be made of any material including plastic, metal or ceramic.

Alternative configurations of accessory patient attachment devices 44 can be used. Patient attachment device 44 can be any length. Patient attachment device 44 can have two clamps or two snaps instead of one of each type of fastener. In one embodiment, a clamp can be used that is spring loaded to provide a desired clamping force. Alternatively the clamp can be made of memory plastic where the memory of the plastic provides the clamping force. Any means for attaching the accessory patient attachment device to the diffusion device and patient, including those disclosed herein and others known to those of ordinary skill in the art. Other examples of suitable connectors include buttons, Velcro® (i.e., hook and look systems), adhesives, and polymeric welds. The patient attachment device may include a strap that wraps around the patient's body rather than attaching directly to clothing.

The present invention also includes kits for delivering supplemental air to a patient using the air diffusion device of the invention. As illustrated in FIG. 7, the kit may include an air diffusion device 10, one or more patient connectors 44a, 44b, and an air supply hose 56. Air supply hose 56 is shown having a female connector 58 that is configured to engage coupling means 32 on inlet stem 22 of device 10. Patient connectors 44a and 44b are configured to attach to device 10 through slits or openings 30. According to other embodiments of kits according to the invention, either the air supply hose 56 or connectors 44 are merely optional.

Device 10 can be made of any material that is compatible with the air supply being used and suitable for use on a person. Examples of suitable materials for making device 10 include polymers and metals. Biocompatible polymers are preferred. An example of a suitable material for manufacturing the diffusion device 10 includes a highly clarified polypropylene random copolymer. According to one embodiment, the diffusion device is advantageously made from a transparent material. Manufacturing device 10 from a transparent material may be advantageous in the case where it is desirable for a health care provider to view the inside of the device (e.g., to check for sputum, emesis or other foreign materials that might block air flow through the diffusion device 22. In one embodiment, the polymer is FDA food grade and does not contain latex.

In a preferred embodiment, diffusion device 10 is manufactured as a single integrated piece including the frustroconicoidal air diffusion body and the inlet stem. A single integrated piece can be achieved by manufacturing the diffusion device using injection molding. Forming the diffusion device as an integral, one-piece unit is advantageous because it eliminates the need to seal the joint between a separately formed coupling device and the inlet stem. Furthermore, an integrally formed coupler eliminates the risk that the coupler will leak or separate from the device during use.

Figure 8A:
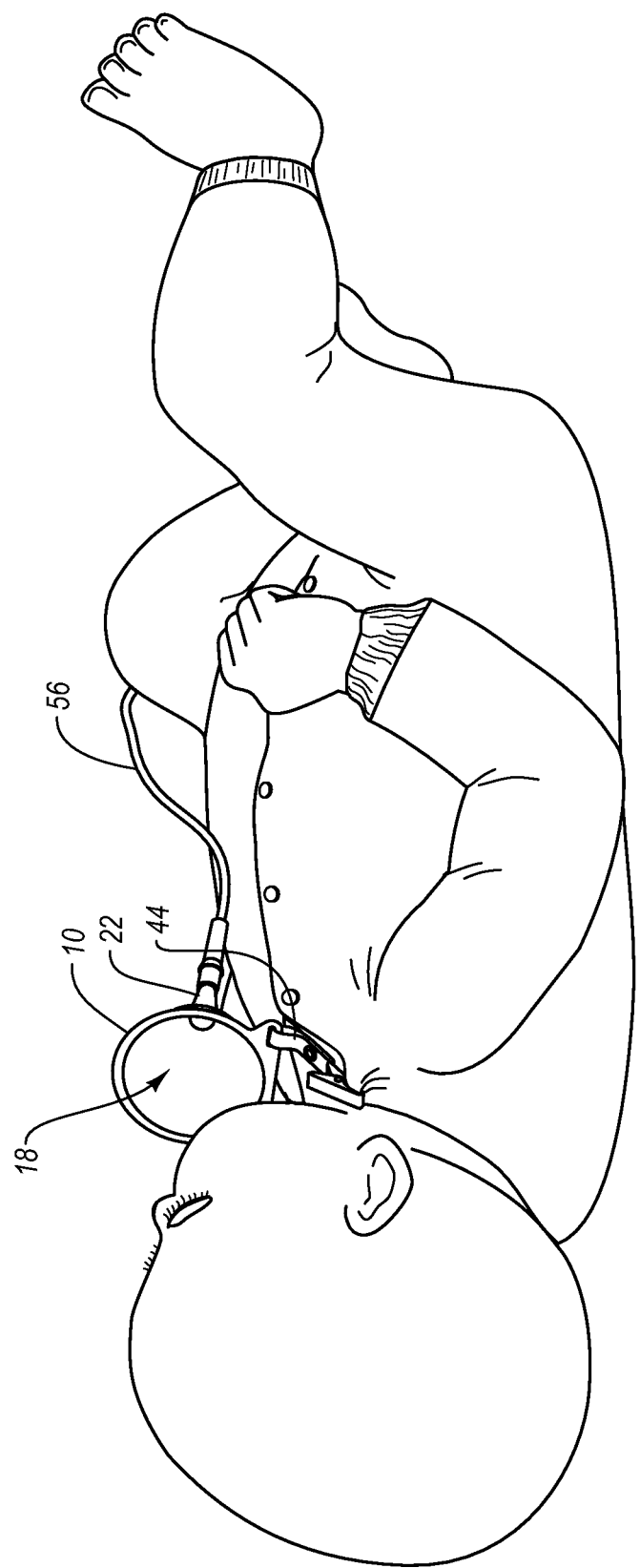
FIG. 8A illustrates a diffusion device attached to an infant's clothing providing supplemental air to the infant.

FIG. 8A shows the use of a supplemental air diffusion device 10, accessory patient attachment devices 44, and air supply hose 56 to provide supplemental air to an infant. Accessory patient attachment devices 44 are connected to respective openings in the flanges extending form an outer surface of device 10. Accessory patient attachment devices 44 are also connected to the clothing of the infant. Device 10 is thereby connected to the infant at a point below the head of the infant, with the diffusion opening 18 positioned so as to direct supplemental air toward the face of the infant. Preferably the diffusion device is attached to the patient with the diffusion opening near the patient's chin such that air is efficiently delivered to the patient's mouth and nose, but not so close to the face so as to bother the infant and trigger a response that would compromise the efficacy of the device.

Air supply hose 56 is connected to the inlet stem of supplemental air device 10. The end of air supply hose opposite device 10 can be connected to any known air supply. In one embodiment, the air supply hose is connected to an air tank with an enriched supply of oxygen. The air tank can include a regulator to release oxygenated air at a desired flow rate and/or at prescribed intervals. The air supply system can also include a nebulizer or other device for introducing a medicament into the air being delivered to the patient.

During use, air supplied by hose 56 enters diffusion device 10 through inlet stem 22 at a relatively high flow rate. The air is diffused as it passes through the frustroconicoidal-shaped body. Because the diffusion opening 18 is much larger than the inlet into stem 22, the flow of air leaving device 10 through opening 18 is much slower than the flow in hose 56. Diffusion opening 18 is sized, shaped, and positioned to deliver the diffused air toward the mouth and nose of the patient. The fasteners on patient connector 44 ensure that the position is maintained during use.

Figure 8B:
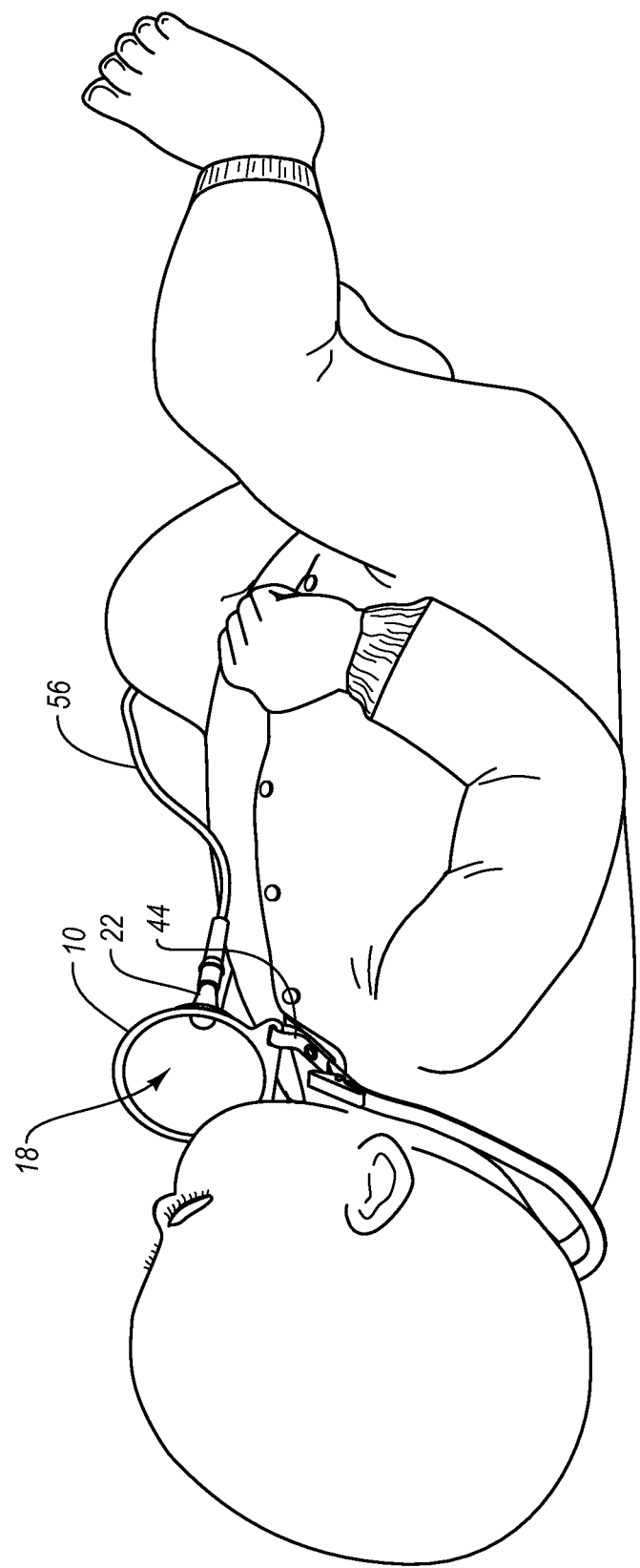
FIG. 8B illustrates a diffusion device attached around an infant's body providing supplemental air to an infant.

FIG. 8B illustrates an accessory patient attachment device that includes an elongate strap that can wrap around and provide direct attachment of the diffusion device to the patient's body.

The diffusion device of the invention allows a health care provider to effectively deliver supplemental air to a patient. Although the diffusion device does not provide a seal around the mouth of the patient, the amount of air can be adjusted to account for supplemental air lost to the surrounding air. The amount of supplemental air delivered to the patient is calculated based on the predicted amount of air lost to the surrounding air. The flow rate can be determined by the health care practitioner.

The present invention advantageously allows a health care provider to deliver a consistent amount of supplemental air to a patient. Because the supplemental air diffusion device connects to the body or clothing of a patient instead of the head, the patient is much less likely to remove the device without permission from the health care provider. The air delivery device of the invention can be safer for a patient to use since the patient is more likely to maintain a supplemental air supply over a longer period of time. In many cases the benefits of maintaining a substantial flow of supplemental air outweigh the disadvantage of not sealing the air diffusion device around the patient's mouth and nose.

The air diffusion device can be positioned in places other than the chest where the patient's position requires a different placement. For example, in some situations, the patient's head may be turned to the side of the body for a lengthy period of time. In this case, the supplemental air diffusion device can be positioned near the shoulder area of the patient to better deliver supplemental air to the patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for delivering supplemental oxygenated air toward a person's face without covering the person's nose and mouth, comprising:
    a supplemental oxygenated air diffusion body made from polymer, metal, or, rigid material and being frustroconicoidal so as to define an interior passageway extending between an inlet end and an outlet end of the diffusion body, the outlet end having an enlarged diffusion opening that is larger than an inlet opening at the inlet end;
    a rigid inlet stem, in fluid communication with the inlet opening, integrally attached to and non-bendably extending from the inlet end of the diffusion body, the inlet stem having a length, diameter, and taper that facilitate insertion into a standard female coupling end of an oxygenated air supply hose;
    one or more ribs or recesses formed on an outer surface of the inlet stem and adapted to mechanically engage an inner surface of the standard female coupling end of the oxygenated air supply hose;
    one or more rigid flanges integrally formed with and extending laterally from an exterior surface of the diffusion body;
    one or more holes or slits formed in the one or more rigid flanges; and
    one or more accessory patient attachment devices adapted for releasable attachment to the one or more rigid flanges of the diffusion device, wherein each patient attachment device includes a strap looped through one of the one or more holes or slits and a spring loaded clamp adapted for removable attachment to clothing.

2. A diffusion device as in claim 1, wherein the one or more rigid flanges are positioned at the outlet end of the diffusion body.

3. A diffusion device as in claim 1, wherein the outlet end of the diffusion body is devoid of any covering over any portion of the enlarged air diffusion opening so as to not obstruct supplemental oxygenated air passing through the enlarged air diffusion opening.

4. A diffusion device adapted for diffusing supplemental oxygenated air toward a person's face without covering the person's nose and mouth, comprising:
    a supplemental oxygenated air diffusion body made from polymer, metal, or rigid material and being frustroconicoidal so as to define an interior passageway extending between an inlet end and an outlet end of the diffusion body, the outlet end having an enlarged diffusion opening that is larger than an inlet opening at the inlet end;
    a rigid inlet stem, in fluid communication with the inlet opening, integrally attached to and non-bendably extending from the inlet end of the diffusion body, the inlet stem having a length, diameter, and taper that facilitate insertion into a standard female coupling end of an oxygenated air supply hose;
    one or more locking ribs or recesses formed on an outer surface of the inlet stem and adapted to mechanically engage an inner surface of the standard female coupling end of the oxygenated air supply hose; and
    first and second spaced-apart patient attachment devices positioned at and directly contacting the outlet end of the diffusion body or one or more rigid flanges integrally formed with and extending from the outlet end of the diffusion body,
    wherein the first patient attachment device includes a first strap looped through a first hole or slit formed in the outlet end of the diffusion body or formed in a first rigid flange, wherein the first patient attachment device further includes a first spring loaded clamp adapted for removable attachment to clothing,
    wherein the second patient attachment device includes a second strap looped through a second hole or slit formed in the outlet end of the diffusion body or formed in a second rigid flange, wherein the first patient attachment device further includes a second spring loaded clamp adapted for removable attachment to clothing.

5. A diffusion device adapted for diffusing supplemental oxygenated air toward a person's nose or mouth without covering the person's nose and mouth, comprising:
    a supplemental oxygenated air diffusion body made from a rigid material and being frustroconicoidal so as to define an interior passageway extending between an inlet end and an outlet end of the diffusion body, the outlet end having an enlarged diffusion opening that is larger than an inlet opening at the inlet end;
    a rigid inlet stem, in fluid communication with the inlet opening, integrally attached to and non-bendably extending from the inlet end of the diffusion body, the inlet stem having a length, diameter, and taper that facilitate insertion into a standard female coupling end of an oxygenated air supply hose;
    one or more locking ribs or recesses formed on an outer surface of the inlet stem and adapted to mechanically engage an inner surface of the standard female coupling end of the oxygenated air supply hose;
    one or more rigid flanges integrally formed with and extending laterally from an exterior surface of the diffusion body;
    one or more holes or slits formed in the one or more rigid flanges and adapted for attachment of one or more accessory patient attachment devices to the one or more rigid flanges; and
    one or more accessory patient attachment devices adapted for releasable attachment to the one or more rigid flanges of the diffusion device, wherein each patient accessory attachment device includes a strap adapted for looping through one of the one or more holes or slits and a spring loaded clamp adapted for removable attachment to clothing.

6. A diffusion device adapted for diffusing supplemental oxygenated air toward a person's nose or mouth without covering the person's nose and mouth, comprising:
- a supplemental oxygenated air diffusion body made from polymer, metal, or rigid material and being frustroconicoidal so as to define an interior passageway extending between an inlet end and an outlet end of the diffusion body, the outlet end having an enlarged diffusion opening that is larger than an inlet opening at the inlet end;
- a rigid inlet stem, in fluid communication with the inlet opening, integrally attached to and non-bendably extending from the inlet end of the diffusion body;
- one or more rigid flanges integrally formed with and extending laterally from an exterior surface of the diffusion body;
- first and second spaced-apart holes or slits formed in the one or more rigid flanges;
- a first patient attachment device including a first strap looped through the first hole or slit and a first spring loaded clamp adapted for removable attachment to clothing,
- a second patient attachment device including a second strap looped through the second hole or slit and a second spring loaded clamp adapted for removable attachment to clothing; and
- a flexible oxygenated air supply hose attached to the inlet stem and including a main, flexible, elongate portion extending beyond the inlet stem.

7. A diffusion device as in claim 6, wherein the supply hose is non removably attached to the inlet stem.

8. A diffusion device as in claim 6, wherein the supply hose is removably attached to the inlet stem.

9. A kit for delivering supplemental oxygenated air to a person toward a person's face without covering the person's nose and mouth, comprising:
- a supplemental oxygenated air diffusion device comprised of:
  - a supplemental oxygenated air diffusion body made from a rigid material and being frustroconicoidal so as to define an interior passageway extending between an inlet end and an outlet end of the diffusion body, the outlet end having an enlarged diffusion opening that is larger than an inlet opening at the inlet end;
  - a rigid inlet stem, in fluid communication with the inlet opening, integrally attached to and non-bendably extending from the inlet end of the diffusion body, the inlet stem having a length, diameter, and taper that facilitate insertion into a standard female coupling end of a flexible oxygenated air supply hose;
  - one or more locking ribs formed on an outer surface of the inlet stem and adapted to mechanically engage an inner surface of the standard female coupling end of the flexible oxygenated air supply hose;
  - one or more rigid flanges integrally formed with and extending laterally from an exterior surface of the diffusion body; and
  - one or more holes or slits formed in the one or more rigid flanges; and
- one or more accessory patient attachment devices adapted for releasable attachment to the one or more rigid flanges of the diffusion device, each accessory patient attachment device having a strap adapted for looping through one of the one or more holes or slits and a snap, velcro or other temporary locking device adapted for selective locking of the strap to itself when looped through the one of the one or more holes or slits, and a spring loaded clamp for selective attachment to clothing.

10. A kit as in claim 9, further comprising the flexible oxygenated air supply hose.

11. A method for delivering supplemental oxygenated air to a patient, comprising:
- providing a kit as in claim 10;
- coupling the flexible oxygenated air supply hose to the inlet opening of the diffusion body and to a supply of oxygenated air;
- attaching the one or more accessory patient attachment devices to the one or more rigid flanges of the diffusion device;
- releasably attaching the diffusion device to clothing or body of the person at a location below the person's face so that the diffusion device does not touch or cover the person's mouth and nose; and
- delivering oxygenated air toward the person's face.

12. A method as in claim 11, where the patient is an invalid, infant, or unconscious person unable to continuously grasp the diffusion device and hold it near the patient's face.

* * * * *